United States Patent
Maschio et al.

(10) Patent No.: US 12,318,343 B2
(45) Date of Patent: Jun. 3, 2025

(54) RETINA MASSAGE AND SMOOTHING DEVICE

(71) Applicant: Alcon Inc., Fribourg (CH)

(72) Inventors: Niccolo Maschio, Winterthur (CH); Reto Grueebler, Greifensee (CH); Timo Jung, Winterthur (CH)

(73) Assignee: Alcon Inc., Fribourg (CH)

( * ) Notice: Subject to any disclaimer, the term of this patent is extended or adjusted under 35 U.S.C. 154(b) by 1042 days.

(21) Appl. No.: 16/884,372

(22) Filed: May 27, 2020

(65) Prior Publication Data

US 2020/0375844 A1 Dec. 3, 2020

Related U.S. Application Data

(60) Provisional application No. 62/854,098, filed on May 29, 2019.

(51) Int. Cl.
| | | |
|---|---|---|
| *A61F 9/007* | (2006.01) | |
| *A61B 17/00* | (2006.01) | |
| *A61H 23/06* | (2006.01) | |
| *A61M 5/00* | (2006.01) | |

(52) U.S. Cl.
CPC ............ *A61H 23/06* (2013.01); *A61B 17/00* (2013.01); *A61F 9/007* (2013.01); *A61F 9/00781* (2013.01); *A61M 5/00* (2013.01); *A61B 2017/00367* (2013.01); *A61H 2201/0153* (2013.01); *A61H 2201/0157* (2013.01); *A61H 2201/1253* (2013.01); *A61H 2205/024* (2013.01)

(58) Field of Classification Search
CPC ............ A61H 23/06; A61H 2201/0153; A61H 2201/0157; A61H 2201/1253; A61H 2205/024; A61B 5/00; A61B 17/00; A61B 2017/00367; A61F 9/007; A61F 9/00781; A61F 9/00727; A61M 5/00
See application file for complete search history.

(56) References Cited

U.S. PATENT DOCUMENTS

| | | | | |
|---|---|---|---|---|
| 4,791,924 | A * | 12/1988 | Kelman | ................. A61B 17/32 606/1 |
| 6,955,809 | B2 * | 10/2005 | Hughes | ................. A61B 90/00 424/93.7 |
| 9,730,834 | B2 | 8/2017 | Charles | |
| 9,962,255 | B1 * | 5/2018 | Weiss | ................. A61F 9/00727 |
| 10,010,447 | B2 | 7/2018 | Kashani | |
| 10,045,883 | B2 | 8/2018 | Egli | |
| 10,500,090 | B2 | 12/2019 | Gunn | |

(Continued)

OTHER PUBLICATIONS

Alcon Global Vitreoretinal Product Catalog, V2, Feb. 2014, pp. 29-47.

*Primary Examiner* — Gary Jackson
*Assistant Examiner* — Sebastian X Lukjan
(74) *Attorney, Agent, or Firm* — PATTERSON + SHERIDAN, LLP (57) ABSTRACT

Particular embodiments disclosed herein provide a retina massage and smoothing device. In certain embodiments, the device comprises a tip configured to be used for manipulating a surface of a retina inside an eye, and a shaft coupled to the tip, the shaft having a proximal end configured to be coupled to a handle, wherein the shaft is further configured to be at least partially housed by an outer tube of the handle.

11 Claims, 5 Drawing Sheets

(56) References Cited

U.S. PATENT DOCUMENTS

| | | | |
|---|---|---|---|
| 2007/0191863 A1* | 8/2007 | De Juan | A61F 9/007 606/108 |
| 2007/0208422 A1* | 9/2007 | Walter | A61F 2/148 623/5.11 |
| 2008/0255578 A1* | 10/2008 | Neusidl | A61F 9/0017 606/107 |
| 2012/0271272 A1* | 10/2012 | Hammack | A61M 5/486 604/257 |
| 2017/0165109 A1 | 6/2017 | Gunn | |
| 2018/0042768 A1 | 2/2018 | Charles | |
| 2018/0104514 A1* | 4/2018 | Gertner | A61H 23/0245 |
| 2018/0296391 A1 | 10/2018 | Charles | |
| 2019/0142635 A1* | 5/2019 | Oberkircher | A61F 9/0017 604/521 |
| 2019/0254705 A1* | 8/2019 | Humayun | A61B 17/02 |

* cited by examiner

RETINA MASSAGE AND SMOOTHING DEVICE

PRIORITY CLAIM

This application claims the benefit of priority of U.S. Provisional Patent Application Ser. No. 62/854,098 titled "Retina Massage and Smoothing Device", filed on May 29, 2019, whose inventors are Niccolo Maschio, Reto Grueebler, and Timo Jung, which is hereby incorporated by reference in its entirety as though fully and completely set forth herein.

TECHNICAL FIELD

The present disclosure relates generally to a retina massage and smoothing device.

BACKGROUND

During certain ophthalmic procedures a surgeon may wish to manipulate the retina. As an example, a surgeon may perform a sub-retinal drug injection for treating macular degeneration that is caused by damage to the macula, which is a region of the retina where vision is most acute. In such procedures, it is important that the injected drug reaches an area below the macula, although an injection in the macula may not be possible. Therefore, the surgeon may perform a sub-retinal injection close to the macula hoping that the injected drug, which is in fluid form, flows under the macula. However, in certain cases, the drug may remain under the retina, in a region adjacent to the macula, and create a fluid bubble (similar to a blister bubble) between the choroid and the retina. In such a situation, the surgeon may wish to press on the bubble to smoothen the surface of the retina and force the fluid to flow to the area under the macula. However, the instruments currently used by surgeons to direct the fluid to the macula are not suitable for that purpose. For example, certain instruments currently used by surgeons may damage the retina, in certain cases.

Another example of why a surgeon may wish to manipulate the retina is for treating macular holes. Macular holes develop when the vitreous pulls away, causing the retina to tear in the macular region. Vitreous is a gel-like substance that takes up about four-fifths of the eye's volume. Massaging the retina in the macular region has been reported by surgeons to be beneficial in treating macular holes. For example, in certain cases, massaging the retina may cause the closure of the macular hole. There are other examples of why a surgeon may wish to manipulate the retina, however, the existing instruments may not be necessarily suitable for such a purpose. Manipulating the retina may include, among other things, touching, massaging, pressing on, and/or smoothing the retina.

BRIEF SUMMARY

The present disclosure relates generally to a retina massage and smoothing device.

Particular embodiments disclosed herein provide a retina massage and smoothing device comprising a tip configured to be used for manipulating a surface of a retina inside an eye and a shaft coupled to the tip, the shaft having a proximal end configured to be coupled to a handle, wherein the shaft is further configured to be at least partially housed by an outer tube of the handle.

The following description and the related drawings set forth in detail certain illustrative features of one or more embodiments.

BRIEF DESCRIPTION OF THE DRAWINGS

The appended figures depict certain aspects of the one or more embodiments and are therefore not to be considered limiting of the scope of this disclosure.

To facilitate understanding, identical reference numerals have been used, where possible, to designate identical elements that are common to the drawings. It is contemplated that elements and features of one embodiment may be beneficially incorporated in other embodiments without further recitation.

DETAILED DESCRIPTION

Figures 1A, 1B, 1C:
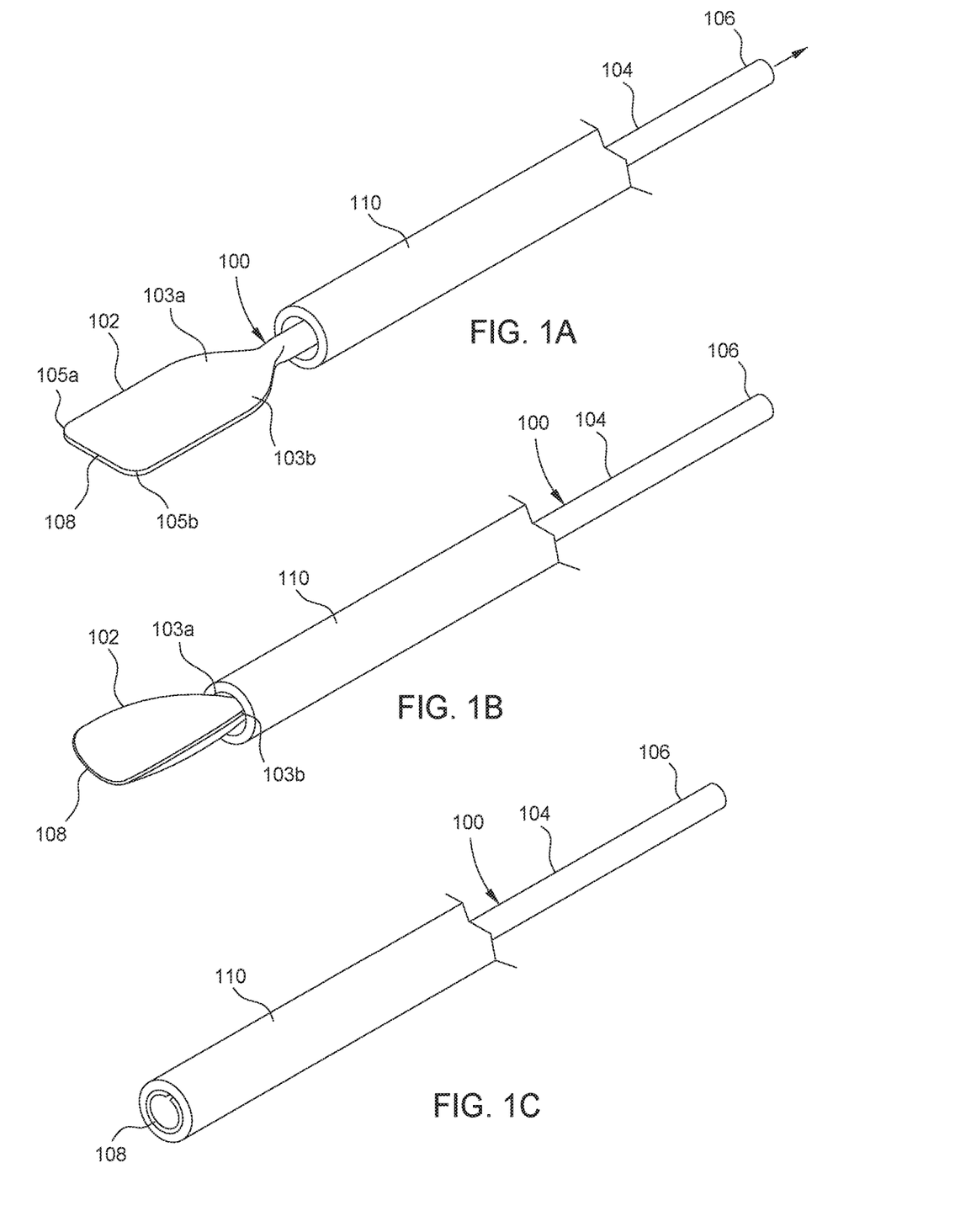
FIGS. 1A-1C illustrate an example of a retina massage and smoothing device in different states, in accordance with certain embodiments of the present disclosure.

Particular embodiments of the present disclosure provide a retina massage and smoothing device. FIGS. 1A-1C illustrate an example of a retina massage and smoothing device ("device") in different states.

FIG. 1A illustrates device 100 including a tip 102 and a shaft 104. The distal end of device 100, which is also the distal end of tip 102, is shown as distal end 108. The proximal end of device 100, which is also the proximal end of shaft 104, is shown as proximal end 106. As used herein, the term "proximal" refers to a location with respect to a device or portion of the device that, during normal use, is closest to the clinician using the device and farthest from the patient in connection with whom the device is used. Conversely, the term "distal" refers to a location with respect to the device or portion of the device that, during normal use, is farthest from the clinician using the device and closest to the patient in connection with whom the device is used.

Figure 2:
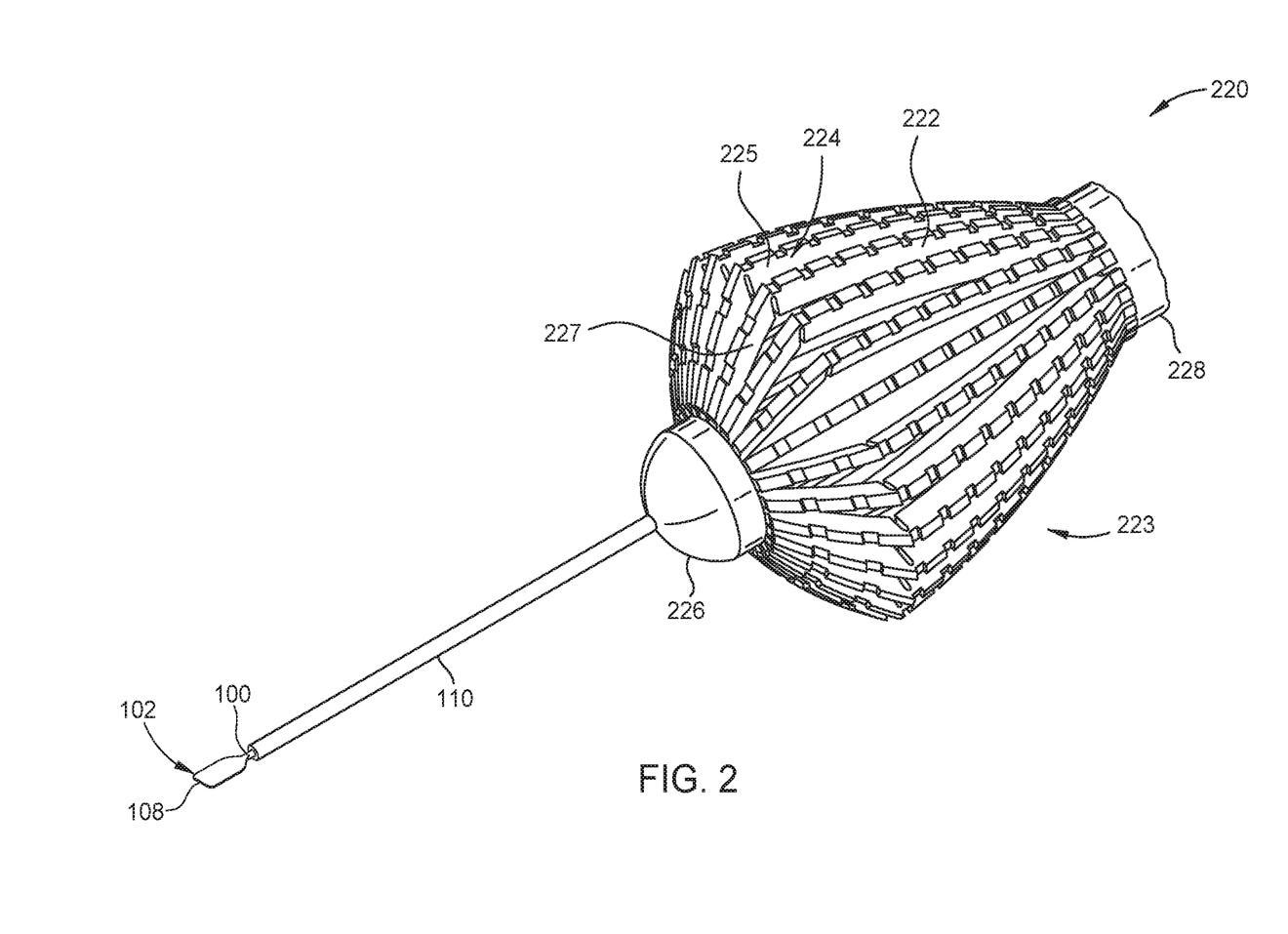
FIG. 2 illustrates an example of a handle to which the device of FIG. 1 may be coupled to, in accordance with certain embodiments of the present disclosure.

As shown, shaft 104 is housed by an outer tube 110 of a handle that is configured to retract and extend device 100. One such suitable handle is the REVOLUTION® DSP handle marketed by Alcon Vision, LLC of Fort Worth, TX. Note that only a portion (distal end) of outer tube 110 is shown in FIG. 1A so that shaft 104 and the proximal end 106 of device 100 are visible. FIG. 2 illustrates a more complete view of outer tube 110 and a handle to which outer tube 110 is coupled.

In certain embodiments, tip 102 is a very thin sheet made of material, such as nitinol, silicone, steel, polyimide, or other similar material. Tip 102 may be referred to as the functional end of device 100 because it is used to manipulate the retina. In certain embodiments, tip 102 includes blunt edges to ensure that manipulating the retina does not cause damage. As shown, tip 102 comprises four corners or vertexes 103a-103b (also referred to as "lower vertexes") and 105a-105b (also referred to as "upper vertexes"). Vertexes 103a-103b are curved and obtuse to ensure that tip 102 is easily retractable, as further described in relation to FIG. 1B.

Tip 102 and shaft 104 may be manufactured as a single element or two separate elements. In embodiments where tip 102 and shaft 104 are manufactured as separate components, one of several techniques may be used to couple tip 102 to shaft 104. For example, the proximal end of tip 102 may be glued to the distal end of shaft 104. In another example, the proximal end of tip 102, which may be needle shaped, is inserted into the distal end of shaft 104. In such an example, the distal end of shaft 104 may provide a hollow opening or compartment that is configured to receive the proximal end of tip 102. The proximal end of tip 102, in such an example, may be friction locked or glued into the hollow opening. Shaft 104 may or may not be made from the same material as tip 102. For example, shaft 104 may be made from materials such as stainless steel, phynox, polyimide, polyetheretherketone (PEEK), etc.

FIG. 1B illustrates device 100 in a partially retracted state. Device 100 is partially retracted when tip 102 is at least partially covered by the distal end of outer tube 110 causing tip 102 to at least partially flex, bend, and/or roll. In FIG. 1B, outer tube 110 has moved in a distal direction in relation to device 100 and is at least partially covering vertexes 103a-103b. As further described in relation to FIG. 2, outer tube 110 may move in a distal direction with respect to device 100 when the handle is at least partially actuated. In certain embodiments, partially retracting device 100 may alter the geometrical shape of tip 102, thereby changing the mechanical attributes of tip 102. More specifically, partially retracting device 100 causes tip 102 to start to bend, flex, and/or roll into outer tube 110, thereby making tip 102 stronger or stiffer along the longitudinal axis of device 100. In certain cases, a surgeon may find that making tip 102 stiffer is beneficial because more force can be applied to the retina during the retina manipulation procedure. Accordingly, by partially retracting device 100, a surgeon is able to make tip 102 stiffer.

As described above, the obtuse and rounded vertexes 103a and 103b allow for retracting device 100 without much friction. If vertexes 103a-b were more acute and sharper, retracting them would result in more friction between tip 102 and the opening at the distal end of outer tube 110.

FIG. 1C illustrates device 100 in a fully retracted state. As shown, outer tube 110 has moved even further in a distal direction with respect to device 100, thereby covering the entire tip 102. Tip 102 is configured to completely bend, flex, and/or roll into outer tube 110 when the handle is fully actuated. A user may fully actuate the handle and place device 100 in a fully retracted state in order to insert outer tube 110 into the eye through an insertion cannula. An insertion cannula is inserted into the eye after making a small incision in the sclera and pars plana. The insertion cannula is configured to allow the user to insert various surgical devices into the eye without causing trauma to the surrounding tissue (e.g., sclera, ciliary, etc.). Retracting device 100 allows the user to insert outer tube 110, and device 100 therein, through the cannula without the tip 102 getting stuck in the insertion cannula or causing damage to the incision in the sclera and ciliary body. Tip 102 is configured or sized such that it can be retracted into an outer tube with a standard size outer diameter (e.g., 20 Ga, 23 Ga, 25 Ga, 27 Ga, etc.).

Note that a partial or full retraction of device 100, as described herein, may result from either outer tube 110 moving towards the distal end 108 of device 100 in relation to device 100 or device 100 being pulled or drawn back into outer tube 110 and toward the proximal end of outer tube 110. In other words, a retraction of device 100, as defined herein, may result from either of the two scenarios or events. Whether device 100 is retracted as a result of outer tube 110 moving in a distal direction in relation to device 100 or as a result of device 100 being pulled or drawn back into outer tube 110 depends on the configuration of the handle to which outer tube 110 is coupled to. FIG. 2 illustrates one example of a handle, which is configured such that device 100 can be actuated as a result of outer tube 110 sliding in a distal direction with respect to device 100.

FIG. 2 illustrates an example of a handle to which device 100 of FIG. 1 may be coupled to. As shown, handle 220 comprises a shaft 228, a basket 223 comprising a plurality of actuation levers 224, a housing 226, an actuation or outer tube 110, and device 100. Although not shown, the proximal end of device 100 (shown as proximal end 106 of FIGS. 1A-1C) is either directly or indirectly coupled to shaft 228. In other words, device 100 is positioned within handle 220 such that device 100 does not move in relation to shaft 228. One or more of several techniques or components may be used to directly or indirectly couple the proximal end of device 100 to shaft 228.

Each actuation lever 224 comprises a first leg 222 and a second leg 227 joined at flexible juncture 225. In other embodiments, the first leg 222 and second leg 227 may be separate pieces coupled together with a hinge. Each actuation lever 224 may be made from shape memory material, such as titanium, stainless steel or suitable thermoplastic. Outer tube 110 may be any suitable medical grade tubing, such as titanium, stainless steel, or suitable polymer and is sized so that device 100 reciprocates easily within.

Handle 220 is designed so that in use, when the plurality of actuation levers 224 are in their relaxed state, device 100 protrudes or extends beyond the distal end of outer tube 110. In the example of FIG. 2, actuation levers 224 are in their relaxed state, in which case, device 100 extends beyond the distal end of outer tube 110. For example, as shown in FIG. 2, tip 102 of device 100 protrudes beyond the distal end of outer tube 110.

Squeezing one or more of the actuation levers 224 causes the respective actuation levers 224 to flex at juncture 225, pushing housing 226 forward relative to shaft 228. The forward movement of housing 226 is transferred to outer tube 110, causing outer tube 110 to slide forward towards the distal end 108 of device 100. FIG. 1B illustrates a partial retraction of device 100, which may result from a user partially (not fully) squeezing one or more of the actuation levers 224. FIG. 1C illustrates a full retraction of device 100, which may result from a user fully squeezing one or more of the actuation levers 224.

FIG. 2 illustrates only one example of a handle that may be used for operating device 100. Other handles that are configured to similarly move outer tube 110 towards the distal end 108 of device 100 in relation to device 100 are also within the scope of the present disclosure. As described above, handles that are configured to pull or draw device 100 back into their respective outer tube are also within the scope of the present disclosure.

Figure 3:
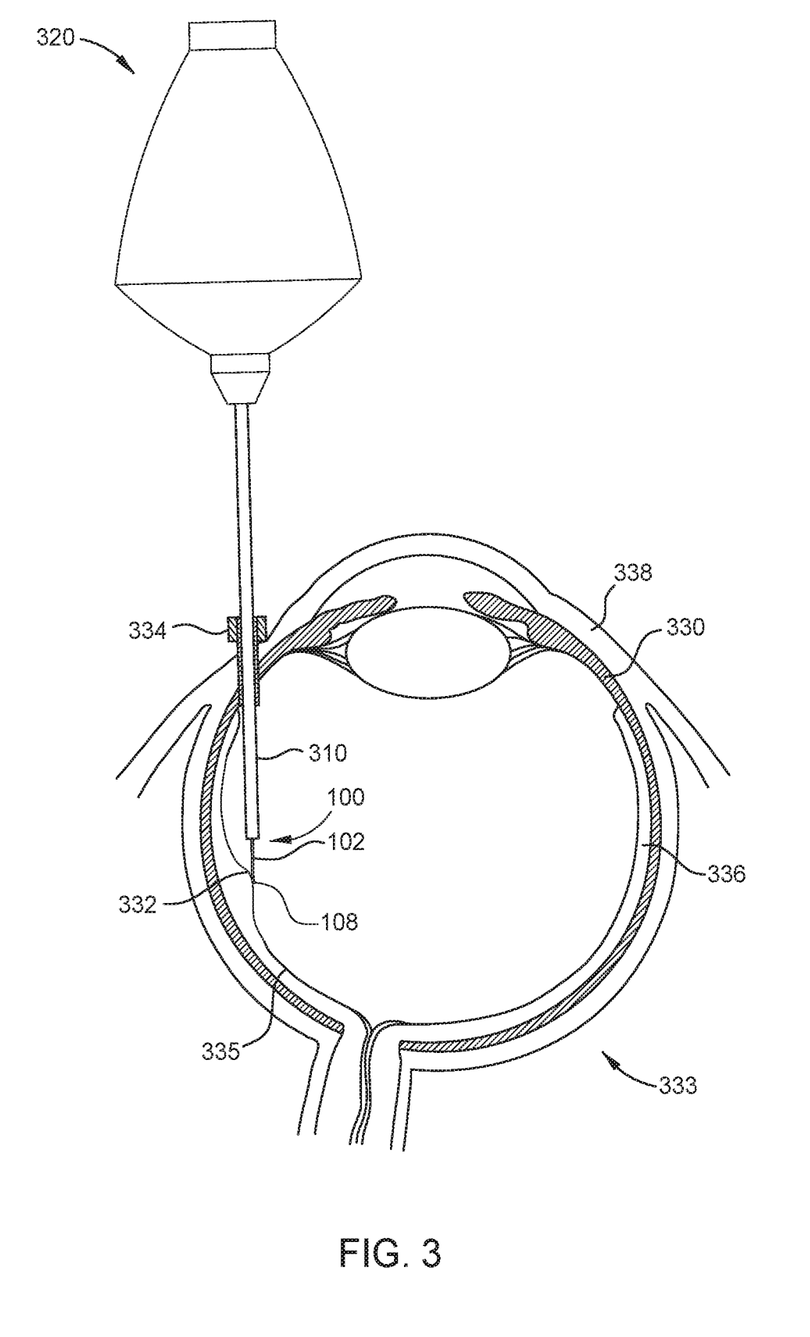
FIG. 3 illustrates an example of the device of FIG. 1 in use, in accordance with certain embodiments of the present disclosure.

FIG. 3 illustrates an example of device 100 in use. As shown, device 100 is used in conjunction with a handle 320 having outer tube 310. Handle 320 may be any handle, such as handle 220, that is able to retract device 100 into outer tube 310. Outer tube 310 is inserted into an eye 333 via an insertion cannula 334. As described above, insertion cannula 334 is configured to allow the user to insert various surgical devices into the eye 333 without causing trauma to the surrounding tissue (e.g., sclera 338, pars plana 330, etc.). Insertion cannula 334 may range from 18 to 27 gauge having a length of 4-8 mm.

Once outer tube 310 is inserted into eye 333, the user may release the actuation levers of the handle, causing tip 102 to roll out of the distal end of outer tube 310. In addition, subsequent to outer tube 310's insertion, the user can move handle 320 to vary the position and depth of outer tube 310 within the eye 333. FIG. 3 shows tip 102 of device 100 from the side. As described above, in certain cases, a sub-retinal drug injection may result in a blister-like bubble 332. To ensure that the drug reaches the macular region 335 of retina 336, a surgeon may use the tip 102 to press on bubble 332 and move the drug that has accumulated under bubble towards macular region 335. In the example of FIG. 3, tip 102 fully extends beyond the distal end of outer tube 310. However, in certain embodiments, the surgeon may find that tip 102 is not stiff enough to apply enough force on bubble 332. In such embodiments, the surgeon may partially retract device 100 and continue to manipulate retina 336 with additional force exerted by a stiffer tip 102 (e.g., shown in FIG. 1B).

Device 100 shown in FIGS. 1-3 is only one example of a device that may be used for a safe and effective manipulation of the retina. FIGS. 4-9 illustrate various types of devices that may be used for retina manipulation by a surgeon.

Figures 4, 5, 6:
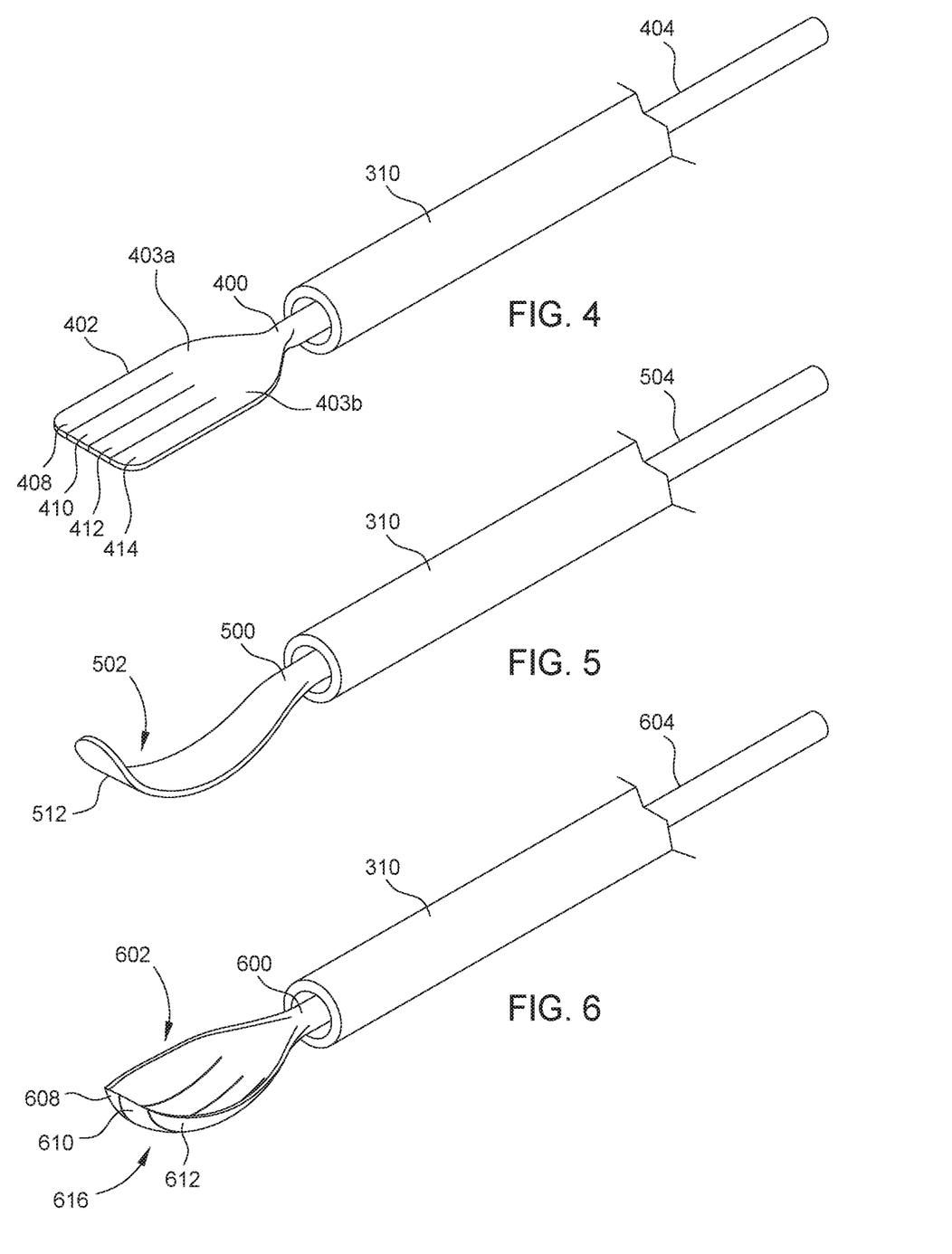
FIG. 4 illustrates an example of a brush-shaped device, in accordance with certain embodiments of the present disclosure.
FIG. 5 illustrates an example of a spoon-shaped device, in accordance with certain embodiments of the present disclosure.
FIG. 6 illustrates an example of a bowl-shaped device, in accordance with certain embodiments of the present disclosure.

FIG. 4 illustrates device 400, which similar to device 100, also comprises a shaft 404 that is inserted within outer tube 310. Device 400 includes a tip 402 having prongs 408, 410, 412, and 414. Prongs 408, 410, 412, and 414 are separable, thereby allowing tip 402 to function like a brush. For example, each of prongs 408, 410, 412, and 414 are functionally coupled at a proximal end of the prongs 408, 410, 412, and 414, but are otherwise not coupled to one another allowing them to move with respect to one another. Accordingly, tip 402, which is sliced, has a lower stiffness than tip 102 of FIGS. 1A-1C, which is a solid sheet. Tip 402 also includes vertexes 403a and 403b, which are obtuse and rounded. Similar to tip 102 of device 100, tip 402 is configured to bend and roll into outer tube 310 when retracted. For example, when tip 402 is being retracted, prongs 414 and 408 may bend and roll over on top of prongs 410 and 412. Partially retracting tip 402 makes tip 402 stiffer, similar to tip 102. Note that in certain embodiments, device 400 may have a larger or smaller number of prongs.

FIG. 5 illustrates device 500, which includes a shaft 504 and a partially hook-shaped tip 502. Tip 502 is curved and has a bottom portion 512, which may be used for manipulating the retina (e.g., pressing on the retina). The curved shaped of tip 502 provides additional flexibility when the bottom portion 512 of tip 502 is pressed against the retina. For example, tip 502 may further bend when it is pressed on the retina. Using device 500, the surgeon may manipulate the surface of the retina by sweeping the bottom portion 512 back and forth on the surface of the retina. Tip 502 is configured to straighten to a degree when device 500 is retracted into outer tube 310.

FIG. 6 illustrates device 600, which includes a shaft 604 and a spoon-shaped tip 602 having separable prongs 608, 610, and 612. Because tip 602 is both spoon-shaped and also includes prongs 608, 610, and 612, it may be referred to as a brush-spoon tip. Also, because of tip 602's prongs 608, 610, and 612, tip 602 has a lower stiffness than a spoon-shaped tip with no prongs. In certain embodiments, tip 602 may be solid instead of having prongs 608, 610, and 612. Similar to tip 502 of device 500, tip 602 also comprises a bottom portion 616, which may be used for pressing the retina. In certain embodiments, prongs 608, 610, and 612 are separable. Note that in certain embodiments, device 600 may have a larger or smaller number of prongs.

Figures 7, 8, 9:
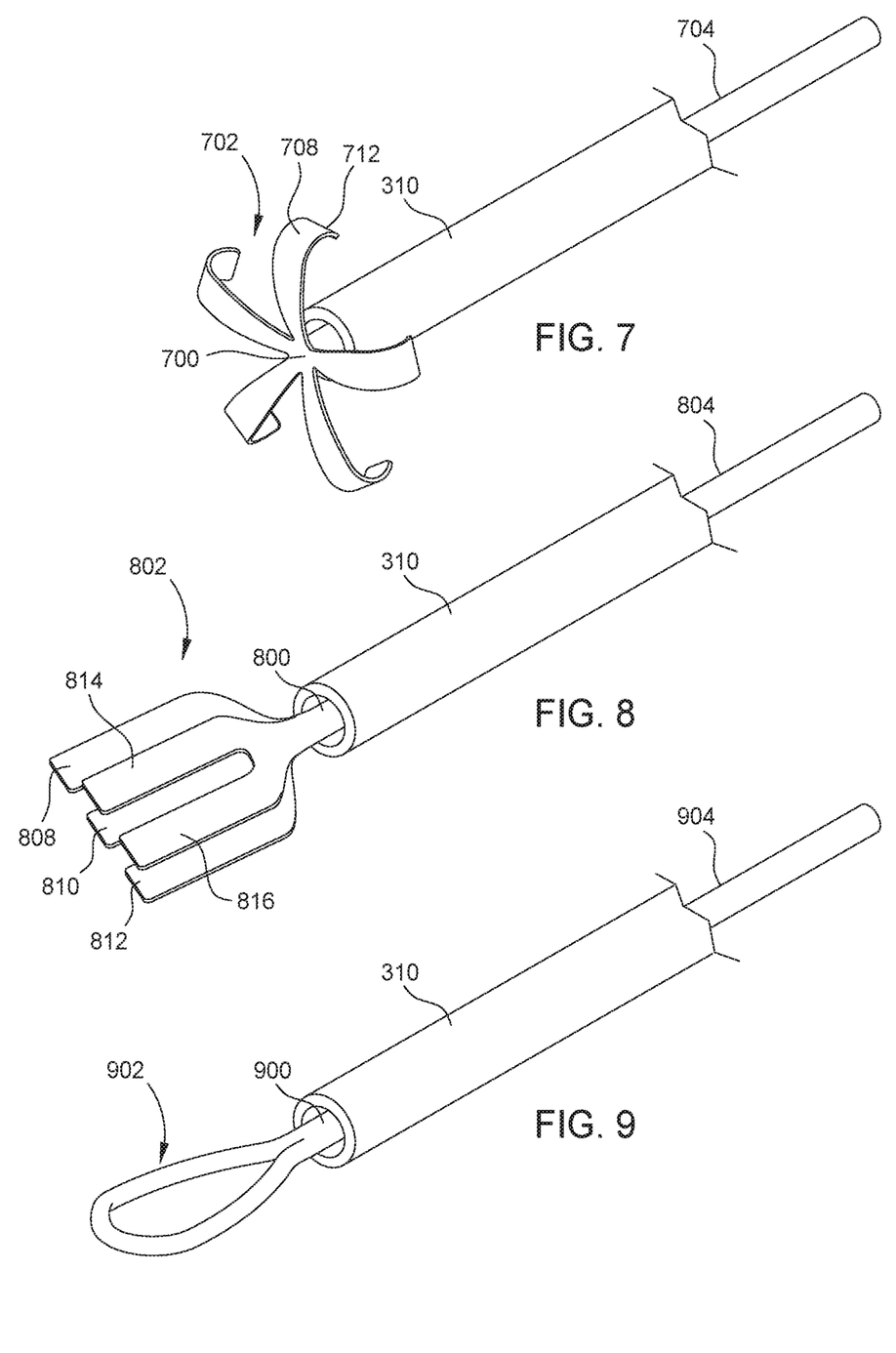
FIG. 7 illustrates an example of an octopus-shaped device, in accordance with certain embodiments of the present disclosure.
FIG. 8 illustrates an example of a brush-shaped device with multiple brush layers, in accordance with certain embodiments of the present disclosure.
FIG. 9 illustrates an example of a loop-shaped device, in accordance with certain embodiments of the present disclosure.

FIG. 7 illustrates device 700 having a shaft 704 and tip 702 that includes a plurality of legs 708 that radiate outward from a longitudinal axis of shaft 704/tip 702. Each leg 708 also comprises a tip 712 that is curved towards the proximal end of shaft 704. Utilizing curved tips 712 ensures that the retina is not damaged in case a tip 712 of one or more of legs 708 makes contacts with the retina. Because of its shape, each leg is also flexible such that pressing legs 708 on the retina results in further bending legs 708 towards the proximal end of shaft 704/outer tube 310. The configuration of tip 702 may be advantageous because legs 708 are able to cover a larger surface area on the retina as compared to tips with other shapes. For example, a surgeon may place all legs 708 of device 700 on top of a blister-like bubble and move the drug that has accumulated underneath it by just pressing tip 702 against the bubble. In such an example, legs 708 may cover a larger surface or portion of the bubble, allowing tip 702 to apply force on the bubble from different sides. Note that in certain embodiments, device 700 may have a larger or smaller number of legs 708.

FIG. 8 illustrates device 800 having a shaft 804 and a brush-shaped tip 802. Tip 802 comprises a first set of separable prongs 814, 816 that is laid on top of the second set of separable prongs 808, 810, and 812. In other words, the first set of separable prongs 814, 816 is adjacent to and in a different plane (e.g., spatial or XYZ plane) than the second set of separable prongs 808, 810, and 812. In the example of FIG. 8, the first set includes two prongs 814, 816 while the second set includes three prongs 808, 810, and 812. However, in other examples, the first set and the second set may each include different numbers of prongs. Because of the two layers of prongs, tip 802 may have a higher stiffness than a brush-shaped tip with only one layer of prongs (e.g., device 400), assuming both tips are made from the same material. In certain embodiments, prongs 808, 810, 812, 814, and 816 are separable. Also note that, in the example of FIG. 8, the first set of separable prongs 814, 816 is shorter in comparison to the second set of separable prongs 808, 810, and 812. Such a configuration may be advantageous because it ensures that the tips of the first set of separable prongs 814, 816 do not extend further than the tips of second set of separable prongs 808, 810, and 812 when tip 802 is bent towards the first set of separable prongs 814, 816. Otherwise, if the first set of separable prongs 814, 816 and the second set of separable prongs 808, 810, and 812 all have the same length, when tip 802 is bent towards the first set of separable prongs 814, 816, the first set of separable prongs 814, 816 may extend further, resulting in a concentration of force at the tips of the first set of separable prongs 814, 816.

FIG. 9 illustrates device 900 having a tip 902 and a shaft 904. Tip 902 is a loop-shaped tip. In addition, tip 902 has curved or rounded edges. Therefore, a surgeon is able to manipulate the retina using device 900 without damaging the retina.

Note that the tips described herein (e.g., tips 102, 402, 502, 602, 702, 802 and 902) may be flexible enough such that when a surgeon presses the tip against the surface of the retina, the tip may flex or bend. In other words, while each of the tips described herein may be stiff enough to manipulate the retina, it is also flexible enough as to not damage the retina. In addition, all of the tips described herein are flexible enough to bend, flex, and/or roll into an outer tube of the handle, as described above.

The foregoing description is provided to enable any person skilled in the art to practice the various embodiments described herein. Various modifications to these embodiments will be readily apparent to those skilled in the art, and the generic principles defined herein may be applied to other embodiments. Thus, the claims are not intended to be limited to the embodiments shown herein, but are to be accorded the full scope consistent with the language of the claims.

What is claimed is:

1. A device, comprising:
    a tip comprising a sheet configured to massage a retina to smooth a bubble between a choroid and the retina or to close a macular hole inside an eye, wherein:
        the sheet comprises separable prongs configured to massage the retina;
        the sheet comprises two lower vertexes and two upper vertexes; and
        the two upper vertexes have a different morphology than the two lower vertexes;
    a shaft coupled to the tip, the shaft having a proximal end configured to be coupled to a handle, wherein:
        the shaft is further configured to be at least partially housed by an outer tube of the handle; and
        the shaft and an entirety of the tip are integrally formed of the same material.

2. The device of claim 1, wherein:
    the two upper vertexes comprise rounded right angles; and
    the two lower vertexes are obtuse and rounded.

3. The device of claim 1, wherein the separable prongs comprise four separable prongs.

4. The device of claim 1, wherein:
    the tip is configured to be partially retracted into the outer tube; and
    the tip is stiffer when it is partially retracted into the outer tube.

5. A device, comprising:
    a tip configured to massage a retina to smooth a bubble between a choroid and the retina or to close a macular hole inside an eye, wherein:
        the tip comprises a spoon-shaped tip, wherein the spoon-shaped tip is segmented to form separable prongs;
        the spoon-shaped tip comprises a concave curvature extending from a proximal end of the tip to a distal end of the tip;
        the separable prongs are configured to adjoin when in a relaxed state to form the concave curvature; and
        a bottom portion of the concave curvature of the distal end of the tip is configured to massage the retina; and
    a shaft coupled to the tip, the shaft having a proximal end configured to be coupled to a handle, wherein:
        the shaft is further configured to be at least partially housed by an outer tube of the handle; and
        the shaft and an entirety of the tip are integrally formed of the same material.

6. The device of claim 5, wherein the separable prongs further comprise three separable prongs.

7. A device, comprising:
    a tip configured to massage a retina to smooth a bubble between a choroid and the retina or to close a macular hole inside an eye, wherein:
        the tip comprises a first set of prongs and a second set of prongs,
        the first set of prongs are adjacent to and in a different plane than the second set of prongs, wherein a portion of the first set of prongs overlaps a portion of the second set of prongs, and
        the first set of prongs comprises a different number of prongs than the second set of prongs; and
    a shaft coupled to the tip, the shaft having a proximal end configured to be coupled to a handle, wherein:
        the shaft is further configured to be at least partially housed by an outer tube of the handle; and
        the shaft and an entirety of the tip are integrally formed of the same material.

8. The device of claim 7, wherein the first set of prongs are shorter than the second set of prongs.

9. The device of claim 7, wherein the tip is configured to be retracted into the outer tube.

10. The device of claim 9, wherein the tip is configured to be retracted into the outer tube by rolling into the outer tube.

11. The device of claim 9, wherein the tip is configured to be retracted into the outer tube by flexing.

* * * * *